(12) United States Patent
Nova et al.

(10) Patent No.: US 6,334,070 B1
(45) Date of Patent: Dec. 25, 2001

(54) VISUAL AND AURAL USER INTERFACE FOR AN AUTOMATED EXTERNAL DEFIBRILLATOR

(75) Inventors: Richard C. Nova, Kirkland; Shawn R. Bertagnole, Seattle, both of WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 0 days.

(21) Appl. No.: 09/444,037

(22) Filed: Nov. 19, 1999

Related U.S. Application Data

(60) Provisional application No. 60/109,168, filed on Nov. 20, 1998.

(51) Int. Cl.⁷ .................................................. A61N 1/39
(52) U.S. Cl. .................................................. 607/5
(58) Field of Search .................. 607/5, 6, 7, 8; 600/523

(56) References Cited

U.S. PATENT DOCUMENTS

| | | |
|---|---|---|
| Re. 34,800 | 11/1994 | Hutchins . |
| 4,583,524 | 4/1986 | Hutchins . |
| 4,619,265 | 10/1986 | Morgan et al. . |
| 5,405,362 | 4/1995 | Kramer et al. . |
| 5,662,690 | 9/1997 | Cole et al. . |
| 5,782,878 | 7/1998 | Morgan et al. . |

FOREIGN PATENT DOCUMENTS

| | | |
|---|---|---|
| 0 555 590 A2 | 8/1993 | (EP) . |
| 0 756 878 A2 | 2/1997 | (EP) . |
| WO 99/24114 | 5/1999 | (WO) . |

*Primary Examiner*—Scott M. Getzow
(74) *Attorney, Agent, or Firm*—Christensen O'Connor Johnson Kindness PLLC

(57) ABSTRACT

An automated external defibrillator (AED) (10) designed for use by a rescuer with minimal or no training during a medical emergency is provided. The AED implements a user interface program (22) which guides the rescuer through operation of the AED and application of CPR and defibrillation therapy to a patient by displaying a series of visual instructions on a graphic display (14) or other visual output device, and by providing additional aural instructions via a speaker (18) or other aural output device. The rescuer merely needs to press a start button (12) to initiate operation of the AED and begin CPR and defibrillation instruction.

47 Claims, 13 Drawing Sheets

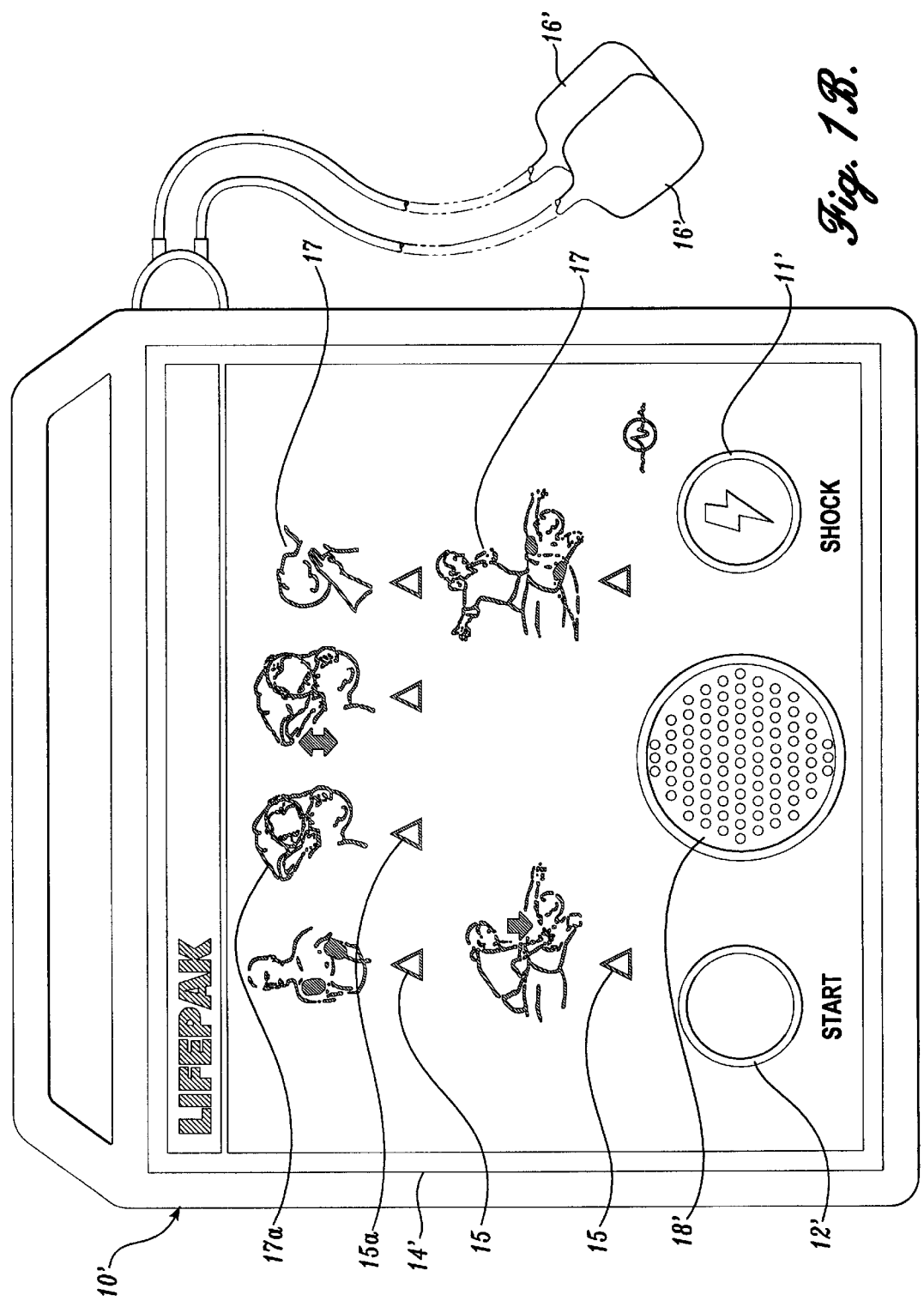

VISUAL AND AURAL USER INTERFACE FOR AN AUTOMATED EXTERNAL DEFIBRILLATOR

RELATIONSHIP TO OTHER APPLICATIONS

This application claims the benefit of U.S. Provisional Application Ser. No. 60/109,168 filed Nov. 20, 1998. The disclosure and drawings of Provisional Application Ser. No. 60/109,168 are specifically incorporated herein by reference.

FIELD OF THE INVENTION

This invention relates generally to defibrillators, and more specifically to portable, automated external defibrillators having a user interface for automatically providing an untrained rescuer with visual and aural instructions for performing emergency cardiopulmonary resuscitation and defibrillation therapy.

BACKGROUND OF THE INVENTION

The probability of surviving a heart attack depends on the speed with which appropriate medical care is provided to the person experiencing the heart attack. To decrease the response time to a patient suffering a heart attack, it has been recognized that those persons who are typically first to arrive at the scene of a medical emergency, including medical technicians (EMTs), firefighters, police and the public (hereinafter collectively referred to as "first responders") should be provided with portable, automated external defibrillators (AEDs). A first responder equipped with an AED will have a greater likelihood of successfully treating the patient than those who arrive later at the scene. An AED designed for first responder use would therefore improve the overall success rate of treating heart attack patients.

Because the probability of surviving a heart attack depends on the speed with which appropriate medical care is provided to the patient, the American Heart Association (AHA) promotes the following "Chain of Survival" guidelines:

(1) Early access to emergency medical service (EMS), such as by activating an emergency response system;

(2) Early CPR initiated by a rescuer to help the patient survive until more advanced care arrives;

(3) Early defibrillation; and (4) Early application of advanced cardiac life support (ACLS), such as airway management, drugs, etc.

With the exception of item number 4, all of the above guidelines can be performed by a first responder with minimal or no training, if provided with sufficient instruction while at the scene.

Even if the first responder does have some basic training in device operation and cardiopulmonary resuscitation (CPR), he or she may forget this basic training during the stress of reacting to a heart attack. With wider deployment of AEDs in homes and public venues, the minimally trained or even untrained use of defibrillation devices will increase. Although some devices already exist for providing CPR prompting and automatic defibrillation therapy, these devices rely on several hours of training experience and verbal cueing for the rescuer to follow. In addition, visual prompting of CPR and defibrillation instructions is achieved only through readable text prompts. Success is diminished due to having to rely on memory recall of CPR and other training protocols. Even retraining and certification every two years is inadequate to ensure proper administration of CPR and defibrillation therapy.

Consequently, a defibrillator is needed which is capable of successfully directing precise instructions to a first responder with minimal or no training through a cardiorespiratory event, i.e., CPR as well as AED device operation, by use of visual and aural instructions. The defibrillator should be as simple and user friendly as possible so as to remove any impediment to use by a rescuer with minimal or no training. Further, the defibrillator should be programmable so as to comply with any changes in the standard protocols for CPR and AED operation.

SUMMARY OF THE INVENTION

In accordance with the present invention, a defibrillator including a user interface for providing a rescuer with instructions for deploying the defibrillator and administrating CPR to a patient is provided. The user interface includes a visual output device for providing the rescuer with visual instructions for deploying the defibrillator and administering CPR to the patient, an aural output device for providing the user with aural CPR and defibrillation instructions, and a user input mechanism for enabling the user to input responses to the visual and aural instructions. The visual and aural output devices of the user interface may also provide the user with visual and aural instructions for notifying an emergency response system of the medical emergency. The visual instructions provided by the visual output device can be animated illustrations, textual prompts, etc., while the aural instructions may be audible tones, verbal prompts, etc. In addition, the user input mechanism may enable the user to skip or repeat instructions. The user input mechanism may be a voice recognition module or a user activated switch or actuator.

In accordance with further aspects of the invention, the defibrillator includes a processing unit coupled to the visual and aural output devices for executing program code stored in memory which generates the emergency notification instructions, CPR instructions and defibrillator operation instructions on the visual and aural output devices. The emergency notification instructions cause the defibrillator to either establish a communication link directly with an emergency response system or cause the defibrillator to instruct the user to notify the emergency response system. The CPR instructions, on the other hand, instruct the user to deliver an appropriate number of breaths and chest compressions to a patient. The defibrillator operation instructions instruct the user to attach the defibrillation electrodes of the defibrillator to the patient and notify the rescuer when a shockable heart rhythm has been detected. In accordance with other aspects of the invention, the memory also stores program code which generates patient assessment instructions which instruct the user to check the patient's breathing and pulse.

In accordance with yet other aspects of the present invention, a method and a computer-executable user interface component are described which provide instructions to a user operating the defibrillator.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1B is a top level view of an AED having a user interface formed in accordance with an alternative embodiment of the present invention;

DETAILED DESCRIPTION OF THE PREFERRED EMBODIMENT

Figure 1A:
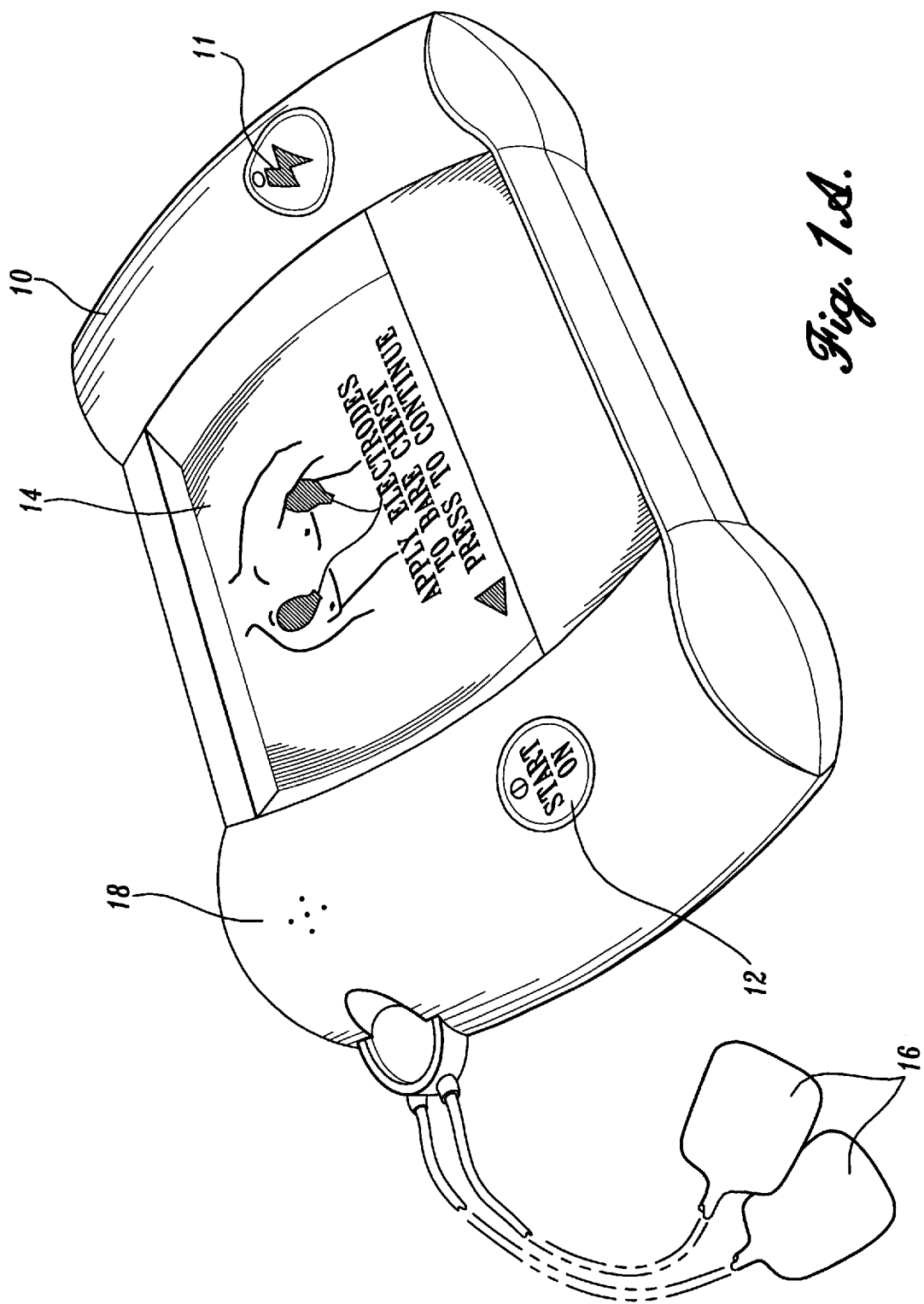
FIG. 1A is an isometric view of an AED having a user interface which automatically provides a rescuer with visual and aural instructions for delivering CPR and/or defibrillation therapy, that is formed in accordance with one actual embodiment of the present invention.

FIG. 1 depicts a portable, automated external defibrillator (AED) 10 formed in accordance with one actual embodiment of the present invention and designed for use by a first responder or rescuer during a medical emergency. The AED 10 stores electric charge and delivers the electric charge to a patient in the form of an electric current pulse, i.e., a defibrillation pulse. The defibrillation pulse is applied to the patient via a set of electrodes 16 if the patient is experiencing a shockable heart rhythm, such as ventricular fibrillation. In the actual embodiment of the present invention depicted in FIG. 1A, the defibrillator 10 guides a rescuer with minimal training or no training whatsoever through operation of the AED and application of CPR and defibrillation therapy to the patient by displaying a series of visual instructions on a liquid crystal display (LCD) 14 and by providing additional aural instructions via a speaker 18. In the actual embodiment of the present invention depicted in FIG. 1A, the rescuer merely needs to press a start button 12 to initiate operation of the defibrillator, and hence, begin CPR and defibrillation instruction.

FIG. 1B illustrates an AED 10' formed in accordance with another actual embodiment of the present invention. In this embodiment, the display 14' comprises a number of illustrations 17 fixed to the top surface of the AED 10' and a light-emitting diode (LED) 15 corresponding to each visual illustration 17. Accordingly, as the rescuer is instructed to perform certain actions, the LED 15 beneath the visual illustration of that action is illuminated. For example, when the rescuer is instructed to check the patient's breathing, the LED 15a beneath the visual illustration of the check breathing instruction 17a is illuminated. In yet another actual embodiment of the present invention, the visual instructions for AED operation and CPR are provided on a laminated card or flip chart, which accompany the AED. In such an embodiment, the rescuer would rely more heavily on the aural instructions generated by the AED via the speaker 18 while following visual instructions along on the card or chart. AED 10' also includes a shock button 11' and start button 12'.

Now that the overall design of an AED capable of providing both visual and aural CPR and defibrillation instructions has been discussed, several key AED components will be discussed in more detail. However, since the components of both AED 10 and AED 10' are essentially the same, the description of these components will be made with reference to AED 10 as depicted in FIG. 1A.

Figure 2:
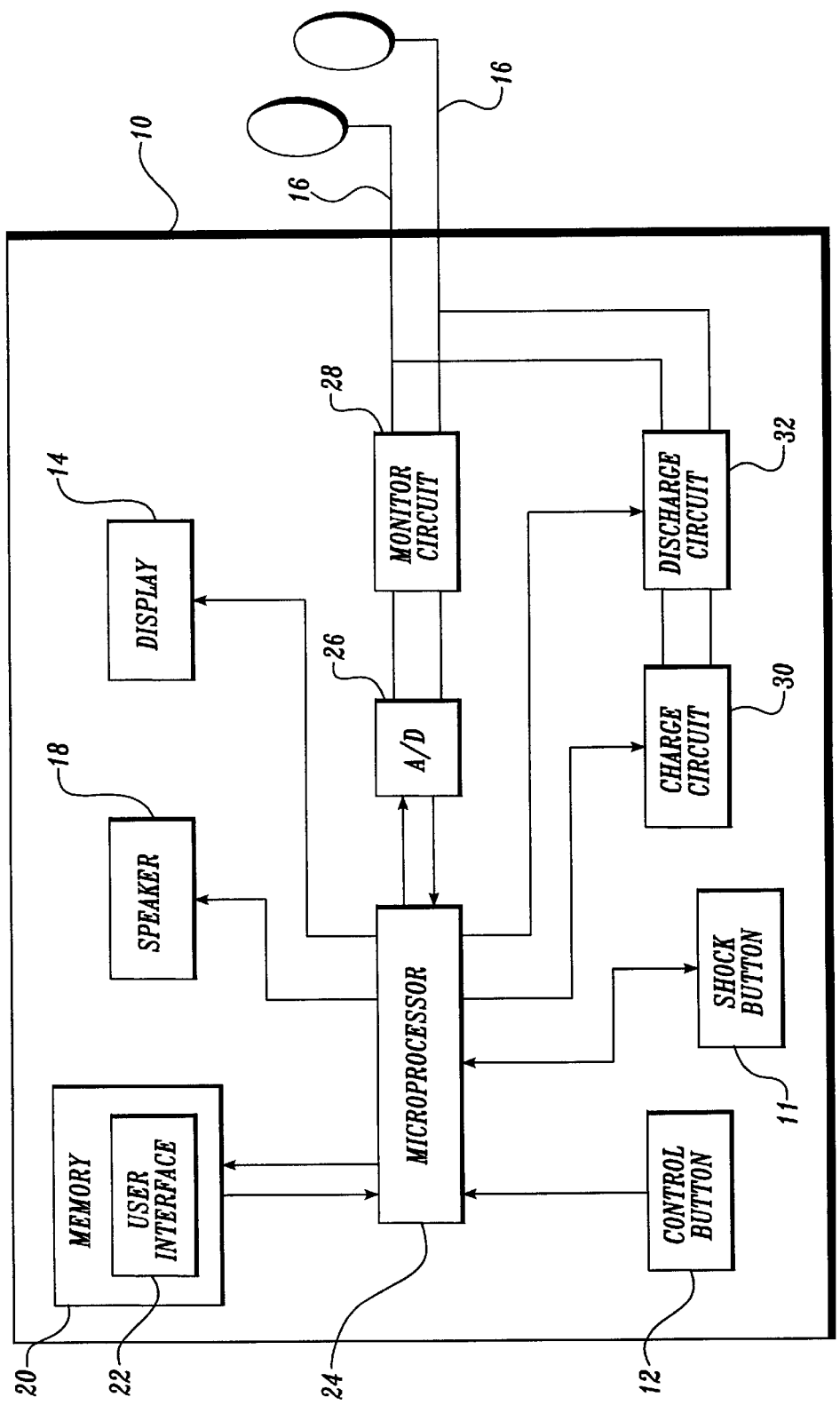
FIG. 2 is a schematic block diagram of several of the key components of the AEDs shown in FIG. 1A and 1B.

As shown in more detail in FIG. 2, the AED 10 includes a microprocessor 24 which controls the operation of the AED 10. The microprocessor 24 is connected to the display 14 (or LEDs 15 of AED 10'), the speaker 18, the start button 12, and the shock button 11. The microprocessor 24 is also connected to a memory 20 which stores a user interface program 22 formed in accordance with the present invention to generate the visual instructions upon the display 14 (or illuminates the LEDs 15 of AED 10') and any accompanying aural instructions transmitted via the speaker 18. In yet other embodiments of the present invention, the memory stores a voice recognition software module which allows the rescuer to operate the AED 10 and respond to visual and/or aural instructions via voice command rather than using the start and shock buttons. Such a module in combination with a microphone would then provide the rescuer with hands-free operation of the AED 10.

During defibrillation operation, the microprocessor 24 analyzes an electrocardiogram (ECG) of a patient using an automatic heart rhythm detection algorithm also stored in memory 20 to identify whether the patient is experiencing a shockable heart rhythm, such as ventricular fibrillation. The detection algorithm executed by the microprocessor 24 in the actual embodiment of the present invention described herein is similar to that used in the LIFEPAK® 500 defibrillator provided by Medtronic Physio-Control Corp. of Redmond, Washington. Other known heart rhythm detection algorithms may also be used without departing from the scope of the present invention, such as those algorithms designed to comply with standards promulgated by the Association for the Advancement of Medical Instruments (AAMI). The ECG signals analyzed by the detection algorithm are collected by the electrode 16 and passed through a monitor circuit 28 to an analog-to-digital converter 26. The analog-to-digital converter 26 then passes the digitized signals to microprocessor 24. If the microprocessor 24 detects a shockable rhythm, the microprocessor causes a charging circuit 30 to generate a current causing a storage capacitor (not shown) to charge in preparation for delivery of a defibrillation pulse. When the capacitor is fully charged, and delivery of the defibrillation pulse initiated, a discharge circuit 32 coupled to the microprocessor 24 and charge circuit 30 discharges the defibrillation pulse to the electrodes 16 for application of the defibrillation pulse to the patient.

In accordance with the present invention, the AED 10 will provide visual and aural instructions to the rescuer via the display 14 and the speaker 18, respectively, advising application of a defibrillation pulse, in which case the rescuer would press a shock button 11 to deliver the defibrillation pulse. However, in another embodiment of the present invention, the AED will automatically apply a defibrillation pulse to the patient if the patient is experiencing ventricular fibrillation, without the rescuer's intervention.

Although the above describes the application of defibrillation therapy to a patient by the AED 10, the AED of the present invention actually provides the rescuer with an intuitive user interface for administering visual and aural instructions necessary for operating the defibrillator to provide defibrillation therapy, as well as instructions for administering CPR. The visual instructions may include inter alia animated or graphic illustrations that flash, move or remain static, textual prompts, light emissions, etc, while the aural instructions may include inter alia verbal prompts audible tones, etc. On a macro level, the user interface can be considered to include the user interface program 22, the display 14 or any other visual output device, generator or mechanism, and the speaker 18 or any other aural output device, generator or mechanism. The user interface of the present invention may also include various user input devices or mechanisms, e.g., shock button 11, start button 12, or voice recognition for allowing the rescuer to input information and/or commands. Since the visual and aural output devices, i.e., display 14 and speaker 18, have already been described, the user interface program 22 of the present invention will be described in more detail in connection with FIGS. 3–9.

Figure 3:
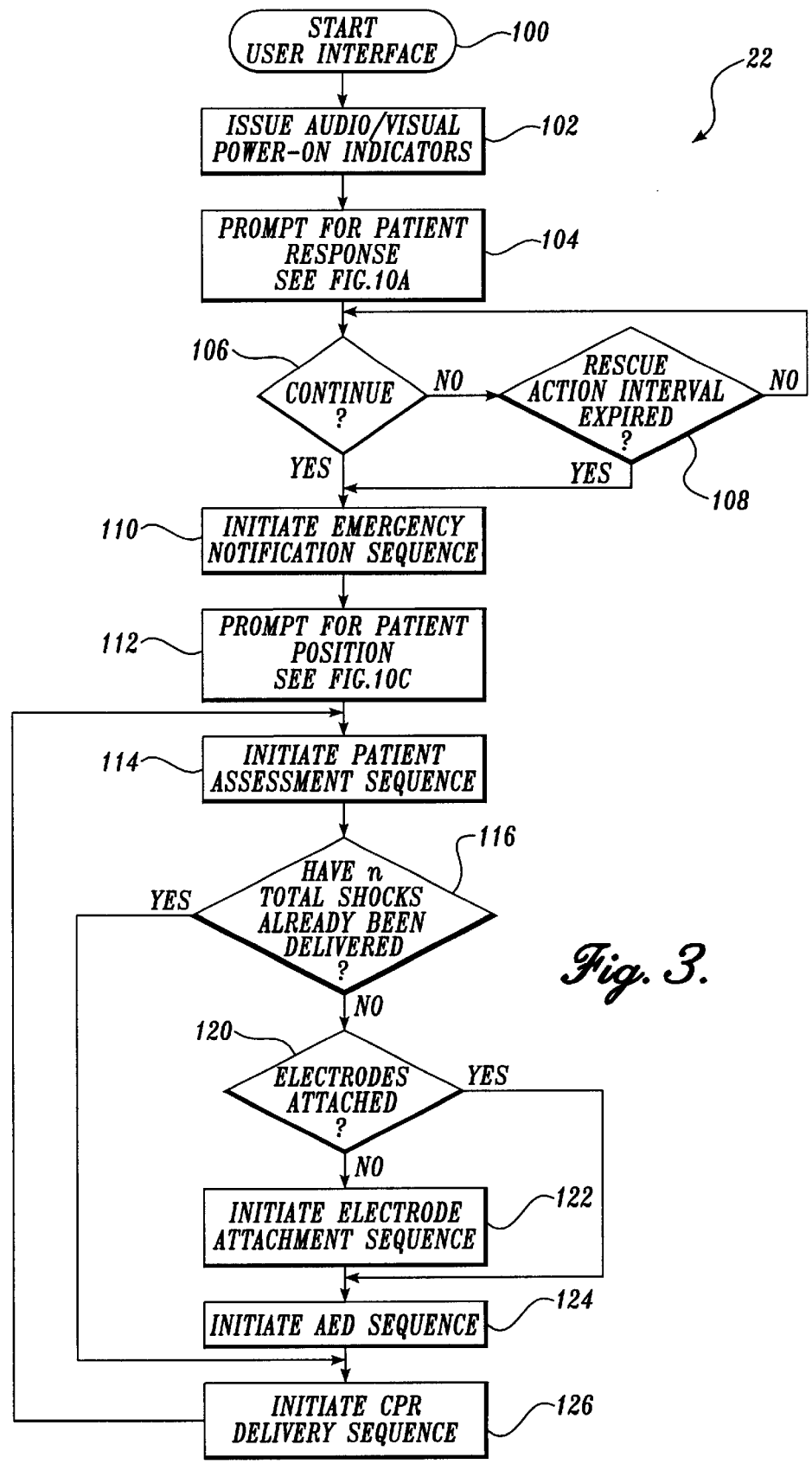
FIG. 3 is a flow chart illustrating the logic used by a user interface program executed by the AED shown in FIG. 1A to provide the rescuer with visual and aural instructions for delivering CPR and/or defibrillation therapy.

FIG. 3 illustrates the logic of the user interface program 22 which is executed by the microprocessor 24 of the AED 10 to provide the rescuer with visual and aural instructions via the display 14 and speaker 18. In order to more fully appreciate the circumstances under which the AED 10 would be used and the advantages of providing a rescuer with visual and aural instructions for providing defibrillation operation/therapy and CPR, it is necessary to discuss the conditions under which the AED 10 would be deployed. Typically, a rescuer would witness or encounter a patient who has collapsed or exhibited some other symptoms associated with cardiac arrest. The rescuer may then attempt to assess the patient and/or call for help, e.g., by calling 911. If available, the rescuer would retrieve the AED 10 and power it on. As described above, the AED 10 is turned on by pressing the start button 12. However, as also noted above, the AED 10 may be powered on by some alternative mechanism or method. It will be appreciated that when the AED 10 is activated, the user interface program 22 is initiated and proceeds as shown in FIG. 3.

Figure 10A:
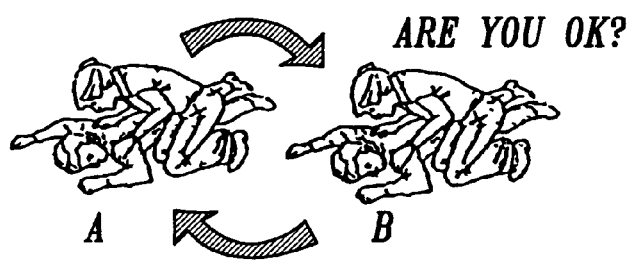
FIGS. 10A–10J illustrate a number of visual instructions provided by the AED in accordance with the present invention.

The logic begins in FIG. 3 in a block 100 and proceeds to a block 102 where it triggers the device to issue an aural power-on indication to the user via the speaker 18, e.g., a power-on tone or perhaps a voice prompt saying "Power On." In addition, a visual power-on indicator is issued on the display 14. This could include a textual "power-on" prompt on the display 14 or the illumination of an LED. Next, in a block 104, the rescuer is instructed both visually and aurally to check the patient's responsiveness. For example, a visual instruction as shown in FIG. 10A is generated upon the LCD 14 of the AED 10. Simultaneously, the rescuer is issued a verbal instruction via the speaker 18 to "Shake and Shout" the patient and ask "Are You Okay?"

In addition to providing the visual and verbal instructions to check the patient's responsiveness, the user interface program 22 also causes the start button 12 to flash so as to indicate to the rescuer that he or she may press the start button 12 to proceed to the next instruction. The user interface program 22 may further provide a verbal instruction to "Press Start Button to Continue" via the speaker 18.

Accordingly, in a decision block 106, the user interface program determines if the rescuer has elected to continue to the next instruction. In accordance with the present invention, the rescuer may continue to the next instruction, and hence, effect the sequence of instructions generated by the user interface program 22 by pressing the start button 12 a single time. If the rescuer has not pressed the start button 12 to indicate his or her desire to skip to the next instruction, the logic proceeds from decision block 106 to a decision block 108 where it determines if the rescuer's time interval for taking action and continuing to the next instruction has expired. If such time interval has not expired, the logic will merely repeat decision blocks 106 and 108 until the rescuer either presses the start button 12 to continue to the next instruction or until the rescuer action interval expires and the user interface program 22 proceeds to the next instruction automatically without further rescuer intervention.

It will be appreciated by those of ordinary skill in the art that the user interface program 22 may provide the rescuer with the option of continuing to the next instruction by pressing the start button 12 (or by activating some other user input mechanism or device such as another button or a voice command) or by waiting to time-out to the next instruction at any appropriate point during the user interface program 22 or any of its subroutines. However, in an effort to avoid redundancy, decision blocks corresponding to 106 and 108 of FIG. 3 are not repeated in the remaining figures after every such instruction. In addition, it will be appreciated that whenever the rescuer is given the option to continue to the next instruction, a verbal instruction to "Press Start Button to Continue" may be issued via the speaker 18, and the start button 12 may be made to flash. In yet other embodiments of the present invention, the rescuer is not provided the option of continuing to the next instruction on demand. Rather, some or all of the subsequent instructions are generated on a time-out basis. Such an embodiment may be advantageous if completely hands-free operation of the AED 10 or further simplification of the user interface (e.g., elimination of the start and shock buttons) is desired.

Returning to decision blocks 106 and 108, if either is positive, the logic will proceed to a block 110 where an emergency notification sequence is initiated by the user interface program 22. As will be described in more detail below, the emergency notification sequence is a subroutine performed by the user interface program 22 to notify the appropriate emergency response system of the patient's collapse.

Figure 10B:
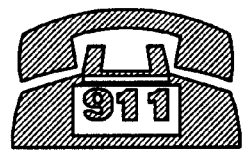

In one actual embodiment of the present invention, the rescuer is instructed by the user interface program 22 to notify the appropriate emergency response system. As will be described in more detail below, in other actual embodiments of the present invention, the AED 10 is programmed to notify the appropriate emergency response system directly. The rescuer initiated emergency notification sequence is depicted in more detail in FIG. 4. The logic begins in FIG. 4 in a block 130 and proceeds to a block 132 where the rescuer is instructed via the display 14 of the defibrillator to call an emergency response system telephone number, such as 911. In the actual embodiment of the present invention described herein, a visual instruction to call 911 as shown in FIG. 10B is generated on the display 14 of the AED 10. A verbal instruction to "Call 911" is simultaneously generated by the speaker 18. Next, in a decision block 134, the user interface program 22 determines if the rescuer has pressed the flashing start button 12 to continue to the next instruction. If not, the logic proceeds to a decision block 136 where it determines if the rescuer's interval for notifying the emergency response system has expired. As noted above, the user interface program 22 will proceed to the next instruction either after the rescuer presses the flashing start button 12 or after the rescuer action interval expires. Consequently, when either of these conditions occurs, the logic in FIG. 4 proceeds to a block 138 and returns to the main user interface program 22 depicted in FIG. 3 so as to proceed to the next instruction for positioning the patient in a block 112.

In another actual embodiment of the present invention, the AED 10 is programmed to notify the emergency response system itself, without human intervention. To do so, those of ordinary skill in the art will recognize that the AED 10 must be equipped with the necessary external interface to communicate with the remote emergency response system. For example, the AED 10 may communicate with the emergency response system via a wireless communication link in which case the external interface of the AED 10 may include an antenna and transceiver for transmitting and receiving radio signals. If communicating via a "wired" communication link, e.g., a "wired" network, a remote telephone/mode connection, a direct port-to-port connection, etc., the AED 10 will be equipped with the appropriate external interface including the necessary circuitry for connecting to the wired communication link and the necessary software for communicating via the appropriate network protocol.

Figure 5:
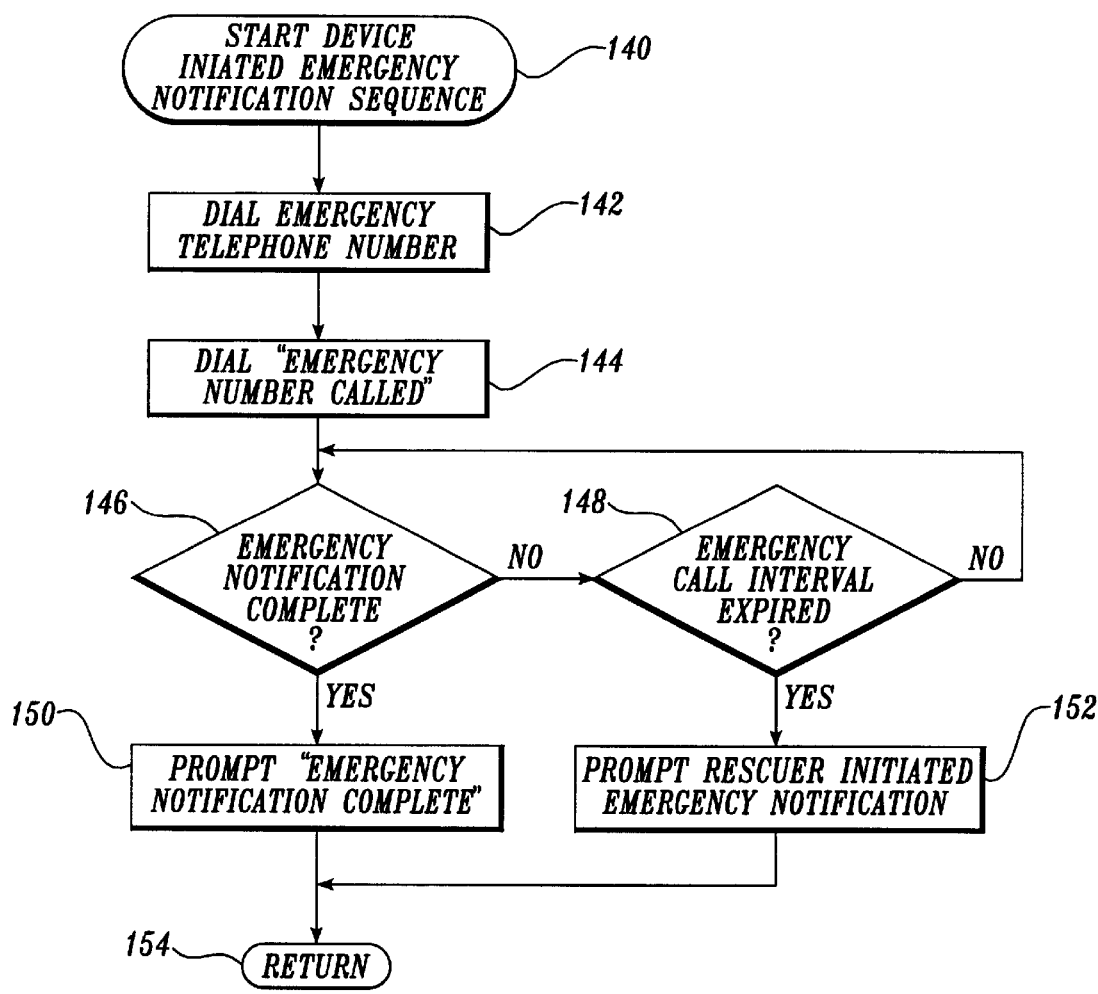
FIG. 5 is a flow chart illustrating the logic used by the user interface program to cause the AED to notify an emergency response system.
Figure 6:
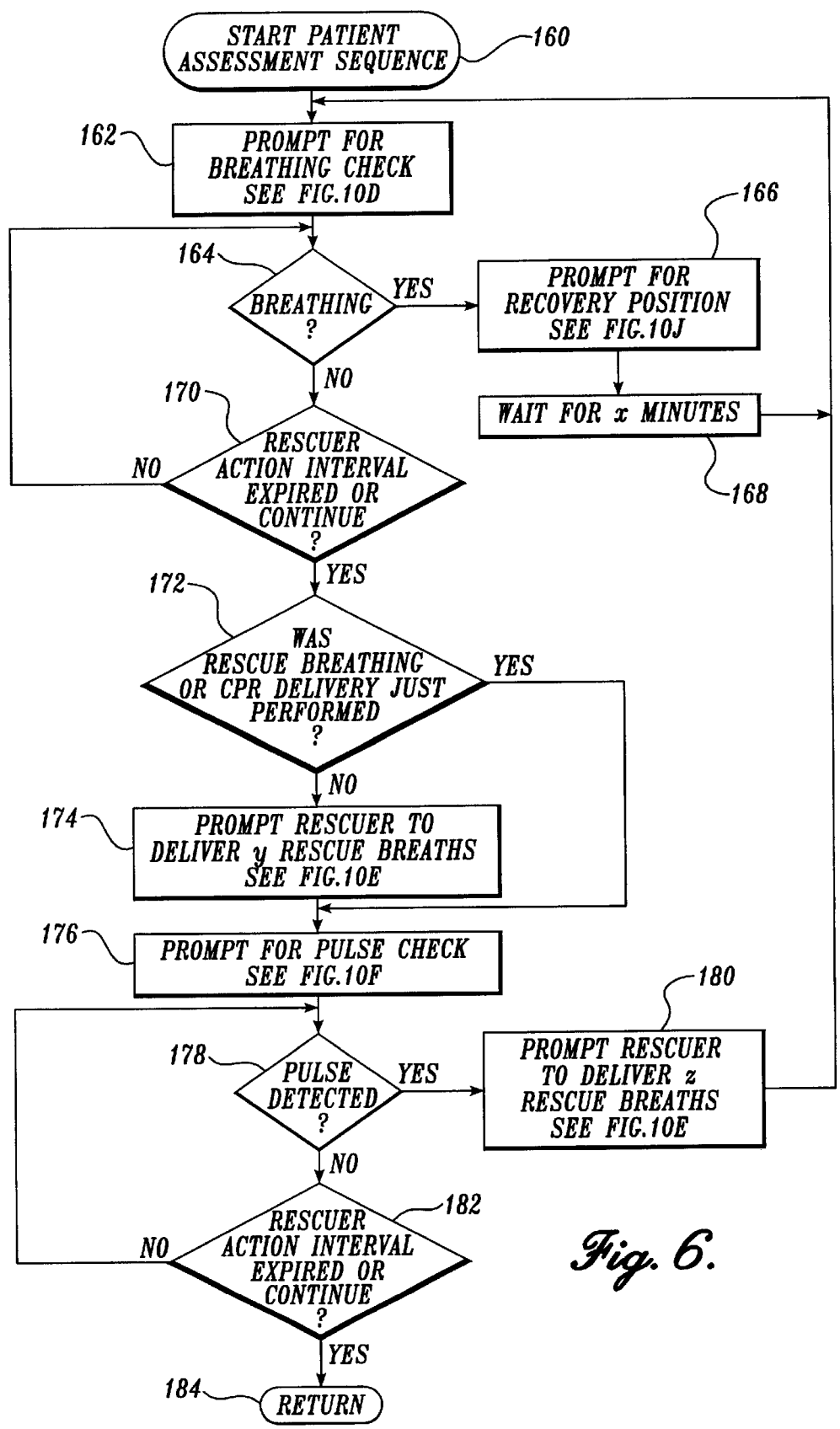
FIG. 6 is a flow chart illustrating the logic used by the user interface program to instruct the rescuer to assess the patient's condition.

The device initiated emergency notification sequence performed by the user interface program 22 is shown in more detail in FIG. 5. Those of ordinary skill in the art will appreciate that in the actual embodiment of the present invention described herein, the device initiated emergency notification sequence is performed as a parallel processing thread to the main user interface program 22. Consequently, the device initiated emergency notification sequence will be performed and the appropriate emergency response system notified while the user interface program 22 continues to provide the rescuer with visual and aural CPR and defibrillation instructions. Accordingly, any visual or aural instructions generated by the device initiated emergency notification sequence will interrupt any currently generated visual or aural instructions provided by the main user interface program 22.

Returning to the substance of FIG. 5, the device initiated emergency notification sequence begins in a block 140 and proceeds to a block 142 where the AED 10 automatically dials a preprogrammed telephone number for the emergency response system, e.g., 911. Accordingly, in a block 144, the user interface program 22 issues via the speaker 18 a verbal instruction confirming that "Emergency Number Called." In addition, a visual, textual instruction of similar nature is generated on the display 14 of the AED 10. Next, in a decision 146 the logic determines if emergency notification has been completed, i.e., that the AED 10 has successfully made a connection with the emergency response system and transmitted preprogrammed information regarding its location to the emergency response system. If emergency notification has not been completed, the logic proceeds to a decision block 148 where it determines if the interval for completing the emergency notification has expired. If not, blocks 146 and 148 are repeated until either the emergency notification has been successfully completed or the emergency call interval has expired.

Figure 4:
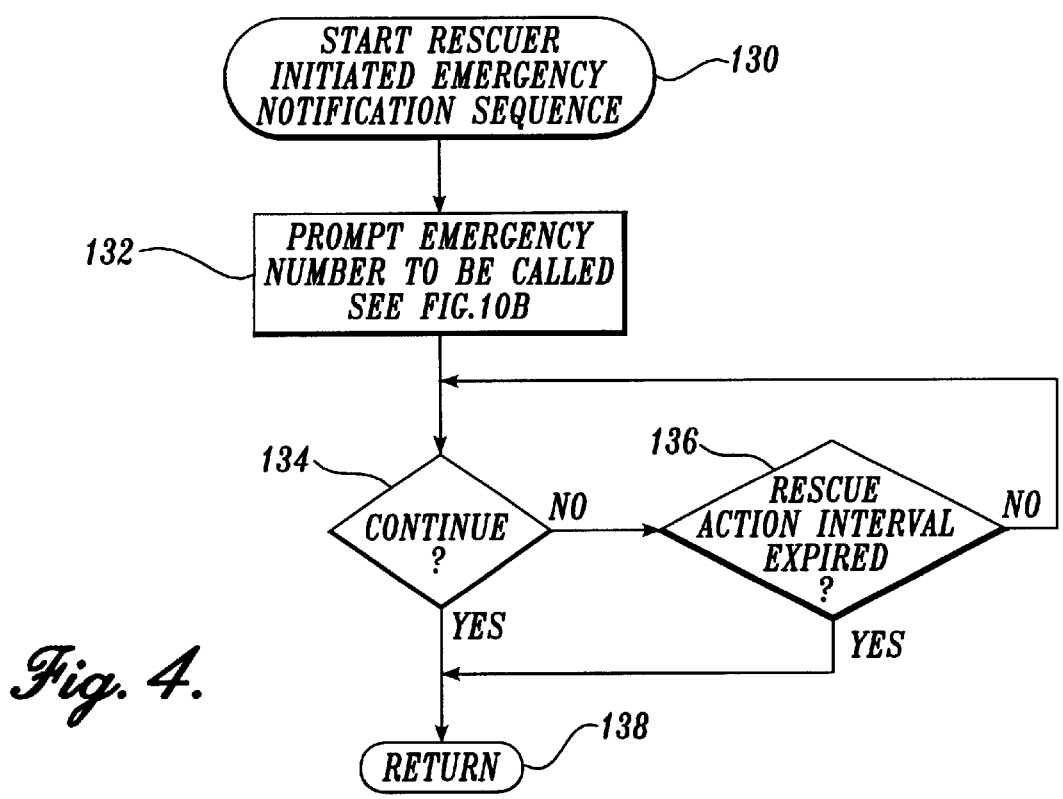
FIG. 4 is a flow chart illustrating the logic used by the user interface program to instruct the rescuer to notify an emergency response system.

Once emergency notification has been completed, the logic proceeds from decision block 146 to a block 150 where a verbal instruction is issued via the speaker 18 confirming that "Emergency Notification Complete." In addition, a textual instruction of similar nature is generated on the display 14 of the AED 10. The logic then ends in a block 154. If emergency notification has not been completed by the AED 10 and the emergency call interval has expired, then the rescuer initiated emergency notification sequence depicted in FIG. 4 is called in a block 152 so that the rescuer is instructed to notify the emergency response in the conventional manner.

It will be appreciated that the emergency response system notified by either the rescuer or the device may be the public emergency response system for local EMS such as police, fire, etc. or a private emergency response system such as a private security or alarm monitoring system. Consequently, the AED 10 is preprogrammed with the appropriate telephone number for the desired emergency response system. In the United States, the public emergency response system is usually notified by calling 911. However, in some remote areas of the U.S. and in many foreign countries different telephone numbers are assigned to the local, public emergency response system.

Finally, in yet other actual embodiments of the present invention, the rescuer or device initiated emergency notification sequence may take place separately from the AED 10. For example, if the AED 10 is deployed from a docking station, the docking station could execute the emergency notification sequence if it were equipped with the necessary hardware and software.

Figure 10C:
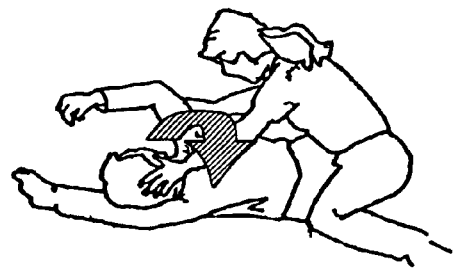

Returning to FIG. 3, following initiation of the emergency notification sequence in block 110, the AED 10 issues visual and aural instructions to the rescuer to place the patient in a proper patient treatment position. For example, the visual instruction depicting proper positioning of the patient as shown in FIG. 10C is generated on the display 14 of the AED 10. At the same time, the rescuer is provided verbal instructions via the speaker 18 to "Turn Victim to Their Back, while Supporting Their Head and Neck." Next, in a block 114, a patient assessment sequence is initiated by the user interface program 22. As noted above, the rescuer may have pressed the start button 12 a single time to proceed to the patient assessment sequence from the patient positioning instruction. Although not depicted in FIG. 3, the rescuer can also repeat the patient positioning instruction (as well as any other instruction provided by the user interface program 22) by pressing the start button 12 twice. In addition, if the rescuer wishes to discontinue operation of the AED 10 completely, the rescuer merely presses the start button 12 and holds it for a predetermined time to power off the AED 10.

Figure 10D:
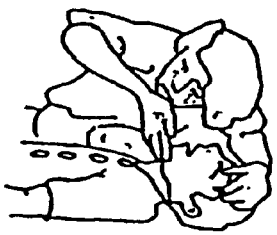
Figure 10E:
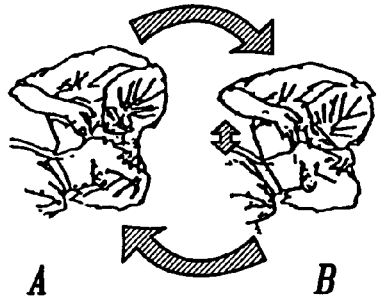
Figure 10F:
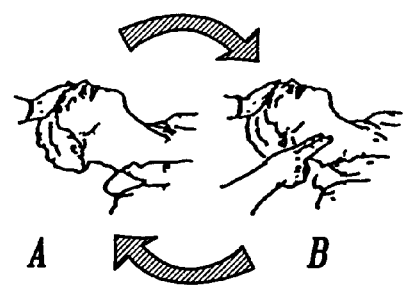
Figure 10G:
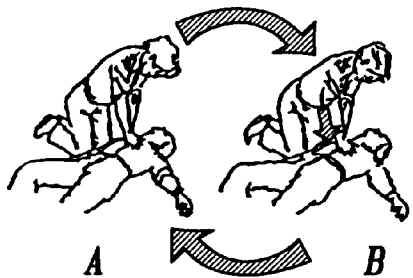
Figure 10H:
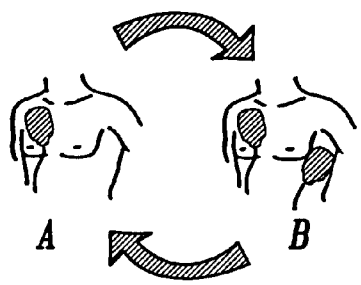
Figure 10I:
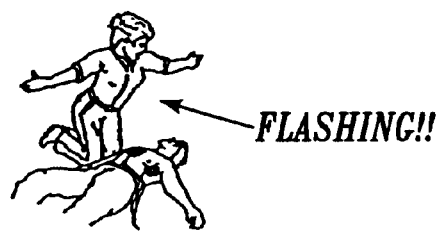
Figure 10J:
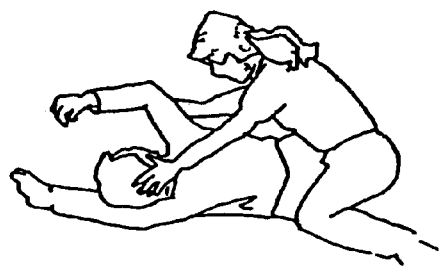

Returning to block 114, the rescuer is instructed to assess the patient's condition once the patient has been placed in the appropriate position. The patient assessment sequence is shown in more detail in FIG. 6. The logic in FIG. 6 begins in a block 160 and proceeds to a block 162 where the user interface program 22 instructs the rescuer to check the patient's breathing. More specifically, a visual instruction to check the patient's breathing as shown in FIG. 10D is generated on the display 14 of the AED 10, while the rescuer is verbally instructed via the speaker 18 to "Tilt Head, Lift Chin" and "Look, Listen and Feel for Breathing." The rescuer is then provided a verbal instruction via the speaker 18 as follows "If Breathing, Press Start Button Once to Continue." Consequently, in decision 164 if it is determined that the patient is breathing, i.e., if the start button has been pressed once, the logic proceeds to a decision block 166 where the user interface program 22 instructs the rescuer to place the patient in the recovery position. More specifically, a visual instruction as shown in FIG. 10J is generated on the display 14 of the AED 10, while the rescuer is verbally instructed via the speaker 18 to "Roll Victim to Their Side If Breathing" and "Stay with Victim Until Help Arrives." Next, in a block 168, the logic waits for a predetermined or x number of minutes, e.g., two minutes, before returning to block 162 and reinitiating the patient assessment sequence.

Returning to decision block 164, if the rescuer does not indicate that the patient is breathing by pressing the start button 12 once, the logic will proceed to a decision block 170 where it determines if the time interval for the rescuer to take action has expired or if the rescuer has pressed the start button 12 two times to proceed to the next instruction. If neither of these conditions have been satisfied, blocks 164 and 170 are repeated until either the rescuer indicates the patient is breathing or until the rescuer action interval expires or the rescuer presses the start button 12 twice to proceed to the next instruction.

Upon expiration of the rescuer action interval or an indication from the rescuer to continue to the next instruction, the logic proceeds to a decision block 172 where it determines if rescue breathing or CPR delivery was just performed. If not, then it is necessary for the AED 10 to instruct the user to deliver rescue breaths before continuing further. To determine whether rescue breathing or CPR delivery was just performed, the user interface program 22 determines whether it has previously instructed the user to deliver rescue breaths as part of the patient assessment sequence or if it has prompted the rescuer to deliver breaths as part of a CPR delivery sequence (described in more detail below) immediately prior to prompting the rescuer to check the patient's breathing. If the result of decision block 172 is positive, the logic proceeds to a block 174 where the AED 10 instructs the rescuer to deliver a predetermined or y number of rescue breaths to the patient where y, for example, is the number of rescue breaths currently recommended under a given standard protocol when a patient is not breathing and a pulse check has not yet been conducted. In accordance with the AHA HeartSaver CPR protocol for adult CPR delivery, this number is presently two. As for generation of the appropriate instruction, the microprocessor 24 of the AED 10 generates a visual instruction as shown in FIG. 10E on the display 14 of the AED 10 and simultaneously causes the speaker 18 to issue a verbal instruction as follows: "If not breathing, give two slow breaths. Tilt, head, lift chin, pinch nose. Blow. (Pause) Blow. (Pause)."

It will be appreciated by those of ordinary skill in the art that following each verbal instruction to "blow," there will be a pause of an appropriate length of time before issuing the next verbal "blow" instruction so as to provide the rescuer with sufficient time to perform the instruction. Under the AHA HeartSaver CPR protocol this pause is 1.5 to 2 seconds. Accordingly, the rescuer is guided to perform the instructed task at appropriate time intervals. Alternatively, rather than repeating the verbal instruction to blow, the speaker 18 may repeat an audible tone at predetermined time intervals to assist the rescuer in executing the blow instruction. Further, the corresponding visual instruction generated on the display 14 may be synchronized with the verbal instruction such that the visual instruction flashes at the same time as the verbal instructions are repeated.

Returning to blocks 172 and 174, after rescue breathing has been performed, the logic proceeds to a block 176 where the rescuer is instructed to check the patient's pulse. More specifically, the user interface program 22 causes the microprocessor 24 to generate a visual instruction to check the patient's pulse as shown in FIG. 10F on the display 14 of the AED 10. Simultaneously, a verbal instruction is issued via the speaker 18 for the rescuer to "Check Pulse." If the rescuer presses the start button 12 to indicate that a pulse has been detected, the logic proceeds to a block 180 where the rescuer is instructed to deliver a predetermined or z number of rescue breaths to the patient, where z, for example, is the number of rescue breaths currently recommended under a given standard protocol when a pulse is detected, but a patient is not breathing. In accordance with the current AHA HeartSaver CPR protocol, the appropriate number of rescue breaths to be delivered when a pulse has not been detected is twelve. The user interface program 22 instructs the microprocessor 24 to generate a visual instruction to deliver rescue breaths as shown in FIG. 10E on the display 14 of the AED 10. A simultaneous verbal instruction is provided via the speaker 18 as follows: "If Not Breathing, Give Twelve Slow Breaths. Tilt Head, Lift Chin, Pinch Nose. Blow. (Pause) Blow. (Pause) Blow . . . . " As noted above, a pause of a length appropriate to allow the user to perform the blow instruction follows each such instruction. For example, under the AHA HeartSaver CPR protocol this pause is five seconds. Upon completion of the visual and verbal instruction to deliver rescue breathing, the logic of FIG. 6 returns to block 162 where the patient assessment sequence is reinitiated and the rescuer is once again instructed to check the patient's breathing.

Returning to decision block 178, if the rescuer does not indicate that a pulse has been detected by pressing the start button 12, the logic proceeds to a decision block 182 where it determines if the rescuer action interval has expired or if the rescuer has pressed the start button 12 twice to continue to the next instruction. If the result of decision block 182 is negative, blocks 178 and 182 are repeated until either a pulse has been detected by the rescuer or until the rescuer action interval has expired or the rescuer has proceeded to the next instruction. In the latter case, if the rescuer action interval expires, or if the rescuer proceeds to the next instruction, it is assumed that a pulse has not been detected. Accordingly, the microprocessor 24 is instructed to return in a block 184 to the main user interface program 22 to a decision block 116 so that further instruction can be delivered to the rescuer for operating the AED 10 and providing defibrillation therapy to the patient, if necessary.

The user interface program 22 determines in decision block 116 if a predetermined or n number of total shocks have already been delivered to the patient, where n is the number of total shocks currently recommended under a given standard protocol. Current standards vary geographically and according to associated medical direction. In some EMS systems, the maximum total number of shocks that may be given to a patient is nine. It will be appreciated, that if the maximum number of shocks have already been delivered to the patient without resulting in successful conversion of the patient's heart to a normal rhythm, that further defibrillation therapy may be fruitless without ACLS intervention. Consequently, if the maximum total number of shocks has already been delivered, the user interface program 22 will instruct the user to deliver CPR in a block 126 rather than repeat the AED operation sequence.

On the other hand, if a maximum total number of shocks has not already been delivered, the logic will proceed from decision block 116 to decision block 120 where the user interface program 22 determines if the electrodes 16 of the AED 10 have been attached to the patient. It will be appreciated that upon initial power-on of the AED 10, the rescuer may not have already attached the electrodes 16 to the patient. Consequently, the AED 10 must instruct the rescuer to do so. Accordingly, the logic proceeds to a block 122 where an electrode attachment sequence is initiated by the user interface program 22. However, if the electrodes have already been attached, the user interface program 22 will skip the electrode attachment sequence and proceed directly to initiating an AED sequence for providing defibrillation therapy in a block 124.

Figure 7:
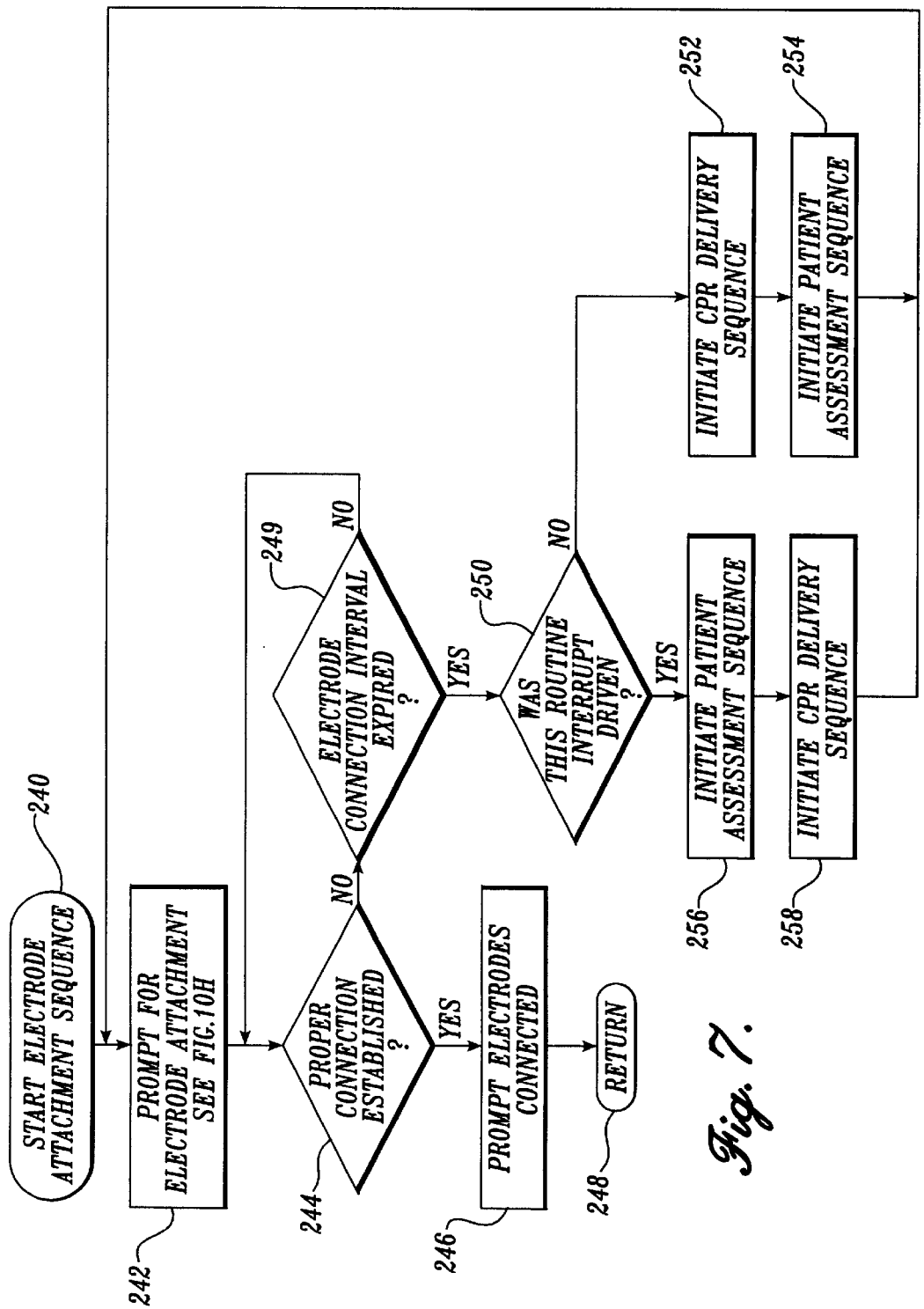
FIG. 7 is a flow chart illustrating the logic used by the user interface program to instruct the rescuer to attach the AED electrodes to the patient.

The logic implemented by the user interface program 22 to perform the electrode attachment sequence is shown in more detail in FIG. 7. The logic of the electrode attachment sequence begins in a block 240 and proceeds to a block 242 where the microprocessor 24 generates the visual instruction for electrode attachment shown in FIG. 10H on the display 14 of the AED 10. Although not shown, if the electrodes 16 are sealed within an electrode package, an additional visual instruction may be displayed for the electrode package opening action. Simultaneously with the visual instruction, a verbal instruction is issued via the speaker 18 to "Apply Adhesive Pads to Bare Chest." Once the instructions have been given for electrode attachment, the logic proceeds to a block 244 where it determines if the electrodes have been properly attached to the patient so that a proper connection between the electrodes and the AED 10 has been established. If so, the AED 10 issues both visual and verbal instructions via the display 14 and speaker 18, respectively, indicating "Adhesive Pads Connected" in a block 246. Next, in a block 248, processing returns to the main user interface program 22 at block 124 where the AED sequence for operating the device to deliver defibrillation therapy is initiated.

Returning to decision block 244, if a proper connection between the patient, electrodes and AED 10 has not been established, the logic proceeds to a decision block 248 where it determines if a time interval allowed for connecting the electrodes 16 to the patient has expired. If not, decision blocks 244 and 248 are repeated until either a proper electrode connection has been established or the electrode connection interval expires. If the electrode connection interval expires without proper connection being established, the logic proceeds to a decision block 250 to determine if the electrode attachment sequence currently being performed was interrupt driven due to detachment of the electrodes from the patient during treatment or if the electrode attachment sequence is being implemented for the first time following deployment of the defibrillator and initial instructions to the rescuer to attach the electrodes. If interrupt driven, it is likely that the electrodes have become detached during CPR delivery or perhaps during the AED sequence. Accordingly, it is prudent for the rescuer to reassess the patient's condition and deliver CPR before attempting to reattach the electrodes. Accordingly, the logic proceeds from decision block 250 to a block 256 where the patient assessment sequence is initiated to instruct the rescuer to again assess the patient for breathing and pulse. Following patient assessment, the logic proceeds to a block 258 where a CPR delivery sequence of instructions described in more detail below is provided to the rescuer. Following patient assessment and CPR delivery, the logic of FIG. 7 returns to block 242 where the rescuer is again provided instructions for attaching the electrodes 16 to the patient.

Returning to decision block 250, if the current electrode attachment sequence was not interrupt driven, i.e., if the sequence was called from the main user interface program 22 in block 122, the logic proceeds from decision block 250 to a block 252 where the CPR delivery sequence is initiated. It will be appreciated that since the electrode attachment sequence was called in this instance for the first time after power-on, patient assessment has just been instructed. Therefore, CPR may be delivered without reassessing the patient. However, following CPR delivery, the patient assessment sequence is repeated in a block 254. The logic then returns to block 242 and the rescuer is instructed once again to attach the electrodes 16 to the patient. As is readily apparent from the above discussion, the electrode attachment sequence may continue indefinitely until proper connection of the electrodes 16 is established. Accordingly, the rescuer will be instructed repeatedly to assess the patient's condition and deliver CPR until emergency assistance arrives.

As noted above, once proper connection of the electrodes 16 has been established, the logic of the main user interface program 22 proceeds to a block 124 where an AED sequence is initiated which instructs the rescuer in proper operation of the defibrillator so as to provide defibrillation therapy to the patient, if necessary. The logic of the AED sequence is shown in more detail in FIGS. 8A and 8B. The logic begins in FIG. 8A in a block 190 and proceeds to a block 192 where an automatic heart rhythm detection algorithm is activated and executed by the microprocessor 24 based on the ECG signals received from the electrodes 16.

Following activation of the automatic rhythm detection algorithm in block 192, the AED 10 notifies the rescuer that analysis has begun and instructs the rescuer to stand clear. More specifically, a visual instruction to stand clear as shown in FIG. 10I is generated by the microprocessor 24 on the display 14 of the AED 10. In addition, the following verbal instruction is issued via the speaker 18: "Analyzing Patient, Stand Clear. Do Not Touch Patient!" After the instruction has been issued, the logic proceeds to a decision block 196 where it determines whether CPR should be delivered prior to any shock. It will be appreciated that certain standard, accepted defibrillation protocols advise that CPR should be delivered before any defibrillation therapy. In the actual embodiment of the present invention described herein, the AED 10 is preprogrammed to require that CPR be delivered preceding a shock in accordance with such accepted protocols. Consequently, the logic automatically proceeds from decision block 196 to a decision block 198 where it determines if a predetermined or j number of CPR cycles CPR has already been delivered to the patient by the rescuer, where j is the number of CPR cycles currently recommended under a given, standard CPR protocol. Current standards vary according to medical direction. In some EMS systems six cycles or ninety seconds of CPR are delivered prior to defibrillation. In other words, the logic determines in decision block 196 whether sufficient CPR has been delivered so that defibrillation therapy may continue. If not, the logic proceeds to a block 202 where processing returns to the main user interface program 22 at a block 126 where the CPR delivery sequence of instructions is initiated.

Returning to decision block 196, in another actual embodiment of the present invention, the automatic rhythm detection algorithm is designed to automatically advise delivery of CPR preceding a shock. If so, the AED sequence will skip the determination of whether a sufficient number of cycles of CPR has been delivered and instead proceed directly to block 202 so processing may resume in the main user interface program 22 with delivery of CPR instructions in a block 126.

Returning to decision block 198, if the appropriate number of CPR cycles has already been delivered, the logic proceeds to a decision block 200 and continues with the AED sequence so that defibrillation therapy may be delivered if necessary. In decision block 200, the logic decides whether a predetermined or n number of consecutive shocks have already been delivered to the patient. Again, in accordance with the current AHA guidelines the maximum number of consecutive shocks allowed is three. If a maximum number of shocks has been delivered consecutively without successful conversion of the patient's heart to a normal heart rhythm, defibrillation therapy will not continue. Rather, processing will return in a block 202 to the main user interface routine so that CPR delivery can be instructed to the user in a block 126. However, if the maximum number of consecutive shocks has not yet been reached, the logic will proceed in FIG. 8A from decision block 200 to a decision block 204 where it determines whether or not the automatic rhythm detection algorithm has detected a shockable rhythm. As those of ordinary skill in the art will recognize, not all abnormal heart rhythms are treatable by defibrillation therapy. However, CPR may still be of benefit to the patient. Accordingly, if a shockable rhythm is not detected, processing will return in block 202 to the main user interface program 22 so that the CPR delivery sequence of instructions may be initiated in a block 126.

On the other hand, if a shockable rhythm is detected in decision block 204, the logic proceeds to a block 205 in which the AED instructs the user verbally that "Shock Advised, Stand Clear." In addition, the microprocessor 24 generates a corresponding visual instruction such as that shown in FIG. 10I on the display 14 of the AED 10. After the rescuer is instructed that a shock has been advised and to stand clear, the AED 10 initiates charge of an energy storage component, e.g., a capacitor, for the device. As those of ordinary skill in the art will appreciate, charging may not be necessary at this point if the energy storage component was precharged and thus, was ready to deliver the shock immediately. However, in the actual embodiment of the present invention described herein, the energy storage component is not, in fact, precharged. Therefore, in a block 208, the AED 10 instructs the user both visually (in text format) and verbally that the energy storage component is "Charging." Next in a decision block 210, the logic determines whether the AED 10 is ready to deliver a defibrillation shock, i.e., whether the energy storage component is fully charged. If not, blocks 208 and 210 are merely repeated until the energy storage component has become fully charged.

Figure 8A:
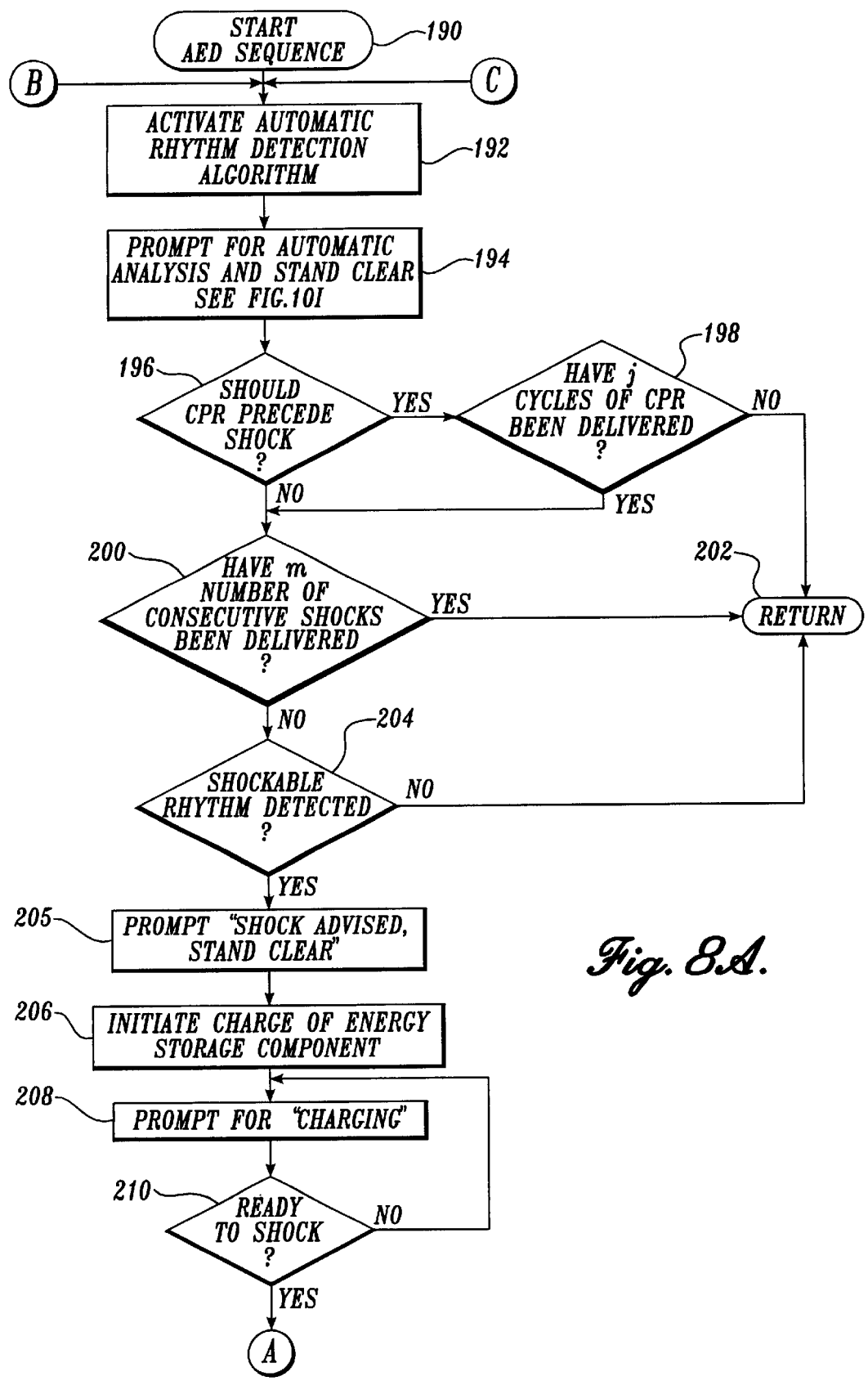
FIGS. 8A and 8B are a flow chart illustrating the logic used by user interface program to instruct the user to operate the AED and deliver defibrillation therapy, if necessary.
Figure 8B:
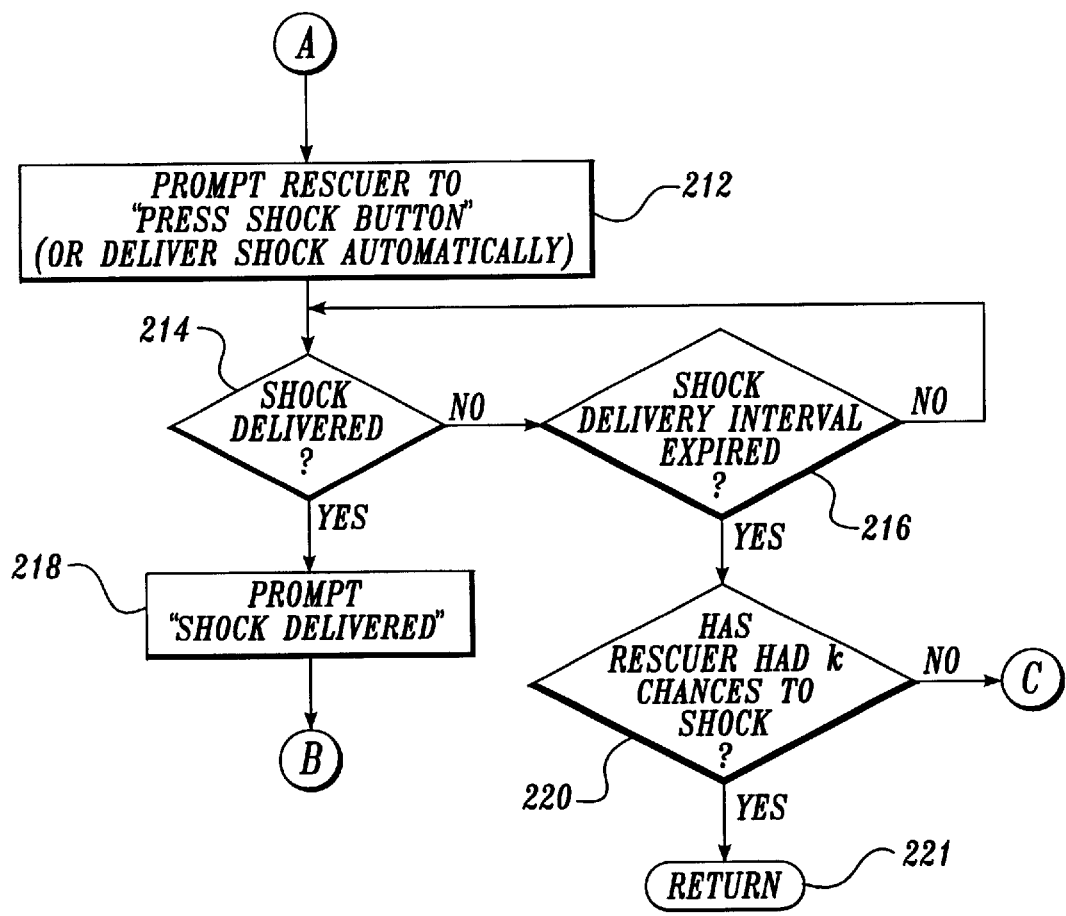
Figure 9:
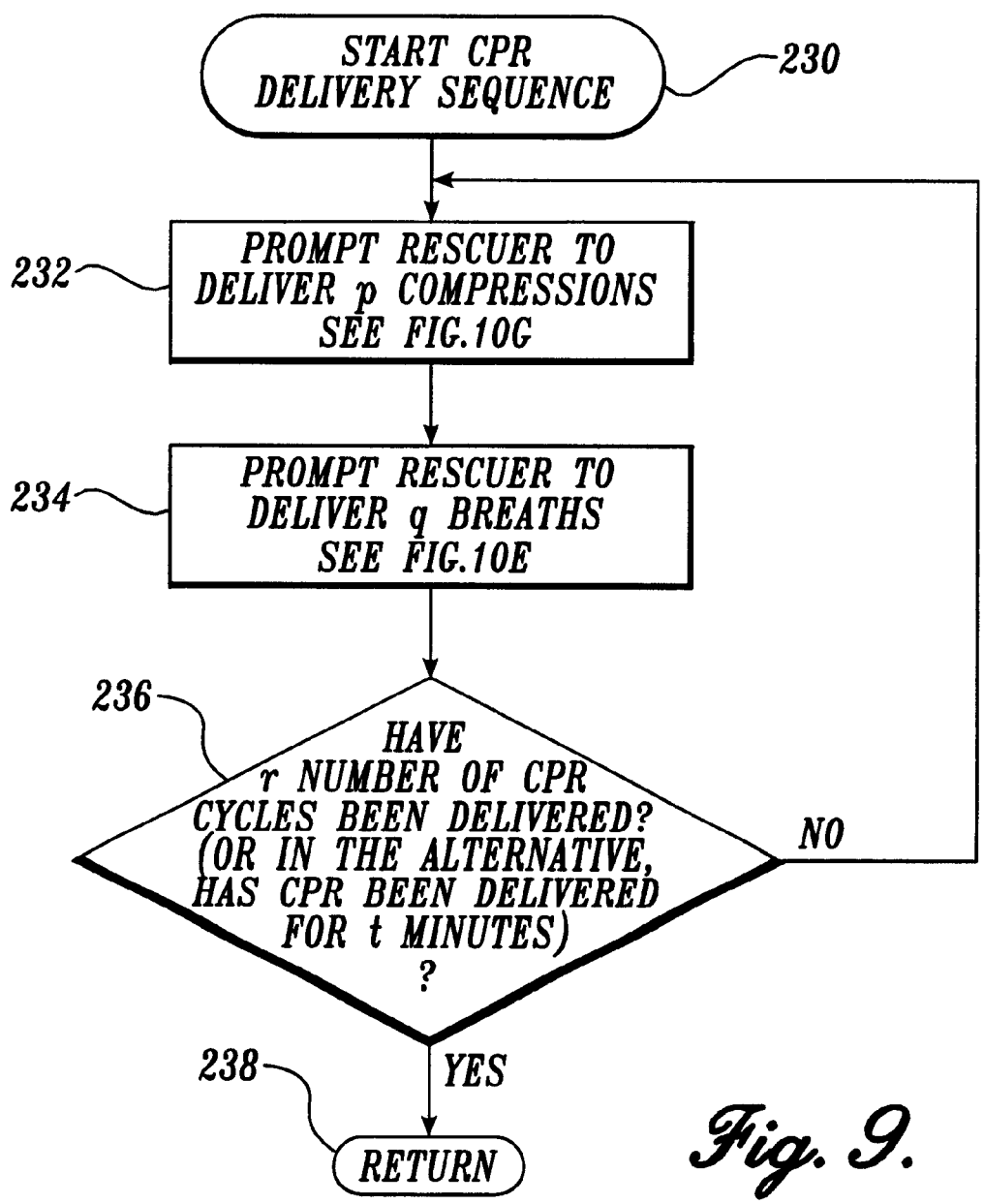
FIG. 9 is a flow chart illustrating the logic used by the user interface program to instruct the rescuer to deliver CPR.

Once the device is ready to shock, the logic proceeds to a block 212 on FIG. 8B in which the rescuer is instructed to "Press Shock Button" in order to trigger delivery of the defibrillation pulse to the patient. Further visual instruction to press the shock button are given to the rescuer by causing the shock button 11 to flash repeatedly. In another actual embodiment of the present invention, the AED 10 is programmed to deliver the shock automatically without further rescuer intervention if a shockable rhythm is detected and the energy storage component is fully charged. In such embodiment, the AED 10 would not include a shock button 11. Regardless of whether the rescuer presses the shock button 11 to initiate the delivery of the defibrillation pulse or whether the AED 10 is programmed to deliver the shock automatically, the logic proceeds from block 212 to a decision block 214 where it determines if the shock has been delivered. If not, the logic proceeds to a decision block 216 where it determines if the shock delivery interval has expired. If not, blocks 214 and 216 are repeated until the shock is either delivered (as initiated by the rescuer pressing the shock button 11 or automatically by the AED 10) or until the shock delivery interval has expired. If the shock is delivered, the rescuer is instructed both verbally and visually that "Shock Delivered." The logic then returns to block 192 on FIG. 8A to reactivate the automatic rhythm detection to determine whether the patient's heart has been converted to a normal rhythm.

If the shock delivery interval has expired before a defibrillation pulse is delivered to the patient, the logic proceeds to a decision block 220 where it determines if the rescuer or AED 10 has had a predetermined or k number of chances to shock the patient. In the actual embodiment of the present invention described herein, the rescuer is given three opportunities to shock the patient. If those three opportunities have not yet been provided, the logic returns to block 192 of FIG. 8A so that the automatic rhythm detection algorithm can be reactivated and the patient's heart rhythm analyzed once again. If the rescuer has had the acceptable number of opportunities to shock the patient but has refrained from doing so, processing returns to the main user interface program 22 in FIG. 3 at a block 126 so that the rescuer may be instructed to deliver CPR to the patient.

Returning now to FIG. 3, after the patient's condition has been assessed by the rescuer, the rescuer has attached the defibrillation electrodes 16 to the patient, and the patient's heart rhythm has been monitored for a shockable heart rhythm such as ventricular fibrillation, the logic proceeds to a block 126 where the CPR delivery sequence is initiated by the user interface program 22. The CPR delivery sequence is shown in more detail in FIG. 9. The logic in FIG. 9 begins in a block 230 and proceeds to a block 232 where the rescuer is instructed to deliver a predetermined or p number of chest compressions to the patient. More specifically, the visual instruction for delivering chest compression shown in FIG. 10G is generated on the display 14 of the AED 10. In the present example, p is the number of compressions required under the AHA CPR protocol for an adult, which is typically 15. In addition to the visual instruction provided by the AED 10, a verbal instruction is provided simultaneously via the speaker 18 to "Place Heel of Hand in Middle of Chest Centered along Nipple Line. Press Firmly 15 Times. Press. (Pause) Press. (Pause) . . . " As discussed above, the pauses between verbal instructions to "Press" are of appropriate length for the rescuer to perform the instruction. Under the AHA HeartSaver protocol, 80 to 100 compressions per minute are recommended. Hence, the rescuer may synchronize his or her actions with the timed verbal instruction.

Once the rescuer has delivered the predetermined number of compressions in block 232, the logic proceeds to a block 234 where the rescuer is instructed to deliver q breaths to the patient, where y is a predetermined number of breaths preprogrammed into the user interface program 22. In the present example, q is the number of breaths required under the AHA CPR protocol for an adult, typically two. The visual instruction for delivery breaths generated by the microprocessor 24 on the display 14 of the AED 10 is shown in FIG. 10E. A verbal instruction to "Tilt head, lift chin, pinch nose. Blow. (Pause) Blow. (Pause)." is then provided simultaneously with the visual instruction shown in FIG. 10E.

Next, in a decision block 236, the logic determines if a predetermined or r number of CPR cycles has been delivered. In other words, the logic determines if blocks 232 and 234 been executed a predetermined number of times. In the actual embodiment of the present invention described herein, r is the number of CPR cycles recommended under the AHA CPR protocol for an adult, typically four. However, it will be appreciated that this number as well as any of the others mentioned above may vary depending on the protocol preprogrammed into the user interface program 22. If the recommended number of CPR cycles has not been delivered, blocks 232, 234 and 236 are repeated until the appropriate number of cycles has been delivered. At that point, processing returns in a block 238 to the routine from which the CPR delivery sequence was called, e.g., user interface program 22, electrode attachment sequence, etc. Those of ordinary skill in the art will appreciate that in other actual embodiments of the present invention, an alternative test for determining when CPR has been sufficiently performed can be implemented in decision block 236. For example, block 236 may determine whether CPR has been delivered for a predetermined time interval t. For example, under the AHA protocol for CPR for an adult, time t is one minute.

Returning to FIG. 3, once the CPR delivery sequence has been performed in block 126, the logic returns to block 116 and blocks 116–126 are repeated indefinitely. Consequently, the user will continuously be instructed to administer CPR and defibrillation therapy until emergency services arrive or until the device is powered down. It will be appreciated that power down could occur by loss of battery or AC power to the AED 10 or by the rescuer pressing the start button 12 continuously for a period of time long enough to distinguish such a button press from a button press which would merely indicate that the rescuer wishes to proceed to the next instruction. In yet other embodiments, power down is achieved by pressing an "off" button.

While a number of actual embodiments of the present invention have been illustrated and described, it will be appreciated that various changes can be made therein without departing from the spirit and scope of the invention. For example, although the user interface program 22 depicted in FIG. 3 is described above in accordance with the actual embodiment of the AED 10 shown in FIG. 1 having an LCD display 14, it will be appreciated that the user interface program 22 may also be implemented by the alternative embodiment of the AED 10' depicted in FIG. 1B with minimal changes. More specifically, rather than generate the appropriate visual instruction on an LCD, visual instructions would be provided to the user by illuminating the LED 15 appearing below the fixed visual instruction 17 as appropriate.

In yet other embodiments of the present invention, the verbal instructions provided to the rescuer simultaneously and in synchronization with the visual instructions could be repeated periodically until the rescuer proceeds to the next instruction. Consequently, the rescuer would continually receive each verbal instruction until the next action is taken. In yet other embodiments, the rescuer could proceed to the next instruction by issuing a voice command to the AED 10 rather than by pressing a button. In such embodiments, the AED 10 would be required to have installed a voice recognition module and microphone as noted above. In yet other embodiments of the present invention, the user interface program 22 can prompt the user to input information regarding the patient that would assist the user interface program in providing more patient specific instructions to the rescuer. For example, the user interface program 22 could generate visual and/or verbal instructions to enter information via the start button 12 to distinguish whether the patient is an adult, child, or infant. Accordingly, the number of chest compressions, rescue breaths, etc. required during CPR delivery and/or the maximum number for total and consecutive shocks would change accordingly.

It will further be appreciated that the visual and aural instructions provided by the intuitive user interface of the present invention may vary from those noted above and illustrated. For example, more information and instruction may be provided to a lay person for clarity and to reduce anxiety. In addition, instructions may be provided with less medical jargon. Accordingly, an even more user friendly user interface is provided. Those of ordinary skill in the art will also recognize that as accepted CPR and defibrillation protocols change, e.g., by adding, deleting or reordering instructions, the AED 10 may be reprogrammed with a simple software upgrade to the user interface program 22 to achieve compliance. For example, the AED 10 may be reprogrammed to add visual and/or aural instructions to unobstruct the patient's airway. Finally, it will be appreciated that any defibrillation device, e.g., a manual defibrillator, a semi-automatic defibrillator or a fully automatic defibrillator, may be equipped with the user interface of the present invention.

The embodiments of the invention in which an exclusive property or privilege is claimed are defined as follows:

1. A defibrillator capable of providing a user with instructions for administering CPR and defibrillation therapy, the defibrillator comprising:
   (a) a processing unit;
   (b) a visual output device coupled to the processing unit for displaying CPR and defibrillation therapy instructions to the user;
   (c) an aural output device coupled to the processing unit for issuing CPR and defibrillation therapy instructions to the user;
   (d) a memory coupled to the processing unit for storing program code executed by the processing unit which generates:
      (i) a sequence of emergency notification instructions on the visual and aural output devices;
      (ii) a sequence of CPR instructions on the visual and aural output devices; and
      (iii) a sequence of defibrillator operation instructions on the visual and aural output devices; and
   (e) a user input mechanism coupled to the processing unit for enabling the user to affect the sequence of emergency notification, CPR and defibrillator instructions, if desired by the user.

2. The defibrillator of claim 1, wherein the sequence of emergency notification instructions comprises instructing the user to notify an emergency response system.

3. The defibrillator of claim 1, wherein the sequence of emergency notification instructions comprises:
   (a) causing the defibrillator to establish a communication link to an emergency response system;
   (b) if the communication link is established, notifying the user that the communication link with the emergency response system has been established; and
   (c) if the communication link fails, instructing the user to notify the emergency response system.

4. The defibrillator of claim 1, wherein the sequence of CPR instructions comprises:
   (a) instructing the user to deliver a predetermined number of breaths to the patient;
   (b) instructing the user to deliver a predetermined number of chest compressions to the patient; and
   (c) instructing the user to repeat the delivery of breaths and chest compressions to the patient.

5. The defibrillator of claim 1, wherein the sequence of defibrillation therapy instructions comprises:
   (a) notifying the user that analysis of the patient's heart rhythm has begun;
   (b) notifying the user when a shockable heart rhythm has been detected; and
   (c) notifying the user when a defibrillation shock has been delivered to the patient.

6. The defibrillator of claim 5, wherein the sequence of defibrillation therapy instructions further comprises instructing the user to deliver the sequence of CPR instructions to the patient if it is determined that CPR should be delivered to the patient before delivering the defibrillation shock to the patient.

7. The defibrillator of claim 5, wherein the sequence of defibrillation therapy instructions further comprises instructing the user to deliver the sequence of CPR instructions to the patient if a predetermined number of consecutive defibrillation shocks have already been delivered to the patient.

8. The defibrillator of claim 5, wherein the defibrillation shock is delivered to the patient automatically when a shockable rhythm has been detected.

9. The defibrillator of claim 5, wherein the defibrillation shock is delivered to the patient when a shockable rhythm is detected and when the user initiates delivery of the shock using the user input mechanism.

10. The defibrillator of claim 1, wherein the program code executed by the processing unit further generates a sequence of electrode attachment instructions.

11. The defibrillator of claim 1, wherein the sequence of electrode attachment instructions comprises:
    (a) instructing the user to attach a set of defibrillation electrodes to the patient; and
    (b) instructing the user to deliver the sequence of CPR instructions to the patient if the defibrillation electrodes have not been attached properly to the patient.

12. The defibrillator of claim 1, wherein the program code executed by the processing unit further generates a sequence of patient assessment instructions.

13. The defibrillator of claim 12, wherein the sequence of patient assessment instructions comprises:
    (a) instructing the user to check the patient's breathing;
    (b) instructing the user to check the patient's pulse; and
    (b) if the patient is neither breathing nor has a pulse, instructing the user to deliver the sequence of CPR instructions to the patient.

14. The defibrillator of claim 13, wherein the sequence of patient assessment instructions further comprises instructing the user to deliver a first predetermined number of rescue breaths to the patient if the patient is not breathing.

15. The defibrillator of claim 14, wherein the sequence of patient assessment instructions further comprises instructing the user to deliver a second predetermined number of rescue breaths to the patient if the patient is not breathing, but the patient's pulse is detected.

16. The defibrillator of claim 15, wherein the sequence of patient assessment instructions further comprises instructing the user to place the patient in a recovery position if the patient is breathing.

17. In a defibrillator, a user interface for providing a user with instructions for deploying the defibrillator and administering CPR to a patient, the user interface comprising:
    (a) a visual output device for providing the user with visual instructions for deploying the defibrillator and administering CPR to the patient, wherein at least some of the visual instructions provided by the visual output device are animated illustrations;
    (b) an aural output device for providing the user with aural instructions for deploying the defibrillator and administering CPR to the patient; and
    (c) a user input mechanism for enabling the user to input responses to the visual and aural instructions provided on the visual and aural output devices.

18. The user interface of claim 17, wherein the visual output device further provides the user with visual instructions for notifying an emergency response system and wherein the aural output device further provides the user with aural instructions for notifying the emergency response system.

19. The user interface of claim 17, wherein the user input mechanism is a voice recognition module.

20. The user interface of claim 17, wherein the user input mechanism is a button actuator.

21. The user interface of claim 17, wherein the user input mechanism enables the user to proceed to a next instruction in response to a current instruction.

22. The user interface of claim 17, wherein the user input mechanism enables the user to repeat an instruction.

23. The user interface of claim 17, wherein at least some of the visual instructions provided by the visual output device are textual prompts.

24. The user interface of claim 17, wherein at least some of the aural instructions provided by the aural output device are repeated.

25. The user interface of claim 17, wherein at least some of the aural instructions provided by the aural output device are tonal prompts.

26. The user interface of claim 17, wherein the aural instructions provided by the aural output device are verbal prompts.

27. A method for providing instructions to a user for operating a defibrillator having a set of electrodes couplable to a patient, wherein the instructions for operating the defibrillator include instructions for administering CPR and defibrillation therapy to the patient, the method comprising:
    (a) causing the defibrillator to instruct the user to attach the set of electrodes to the patient;
    (b) causing the defibrillator to analyze the ECG signals received via the set of electrodes to detect if a shockable heart rhythm is detected;
    (c) causing the defibrillator to instruct the user to deliver CPR to the patient, wherein causing the defibrillator to instruct the user to deliver CPR to the patient comprises:
        (i) determining if the patient is breathing;
        (ii) determining if the patient has a pulse; and
        (iii) instructing the user to deliver a predetermined number of breaths and chest compressions to the patient, if the patient is not breathing and if the patient does not have a pulse; and
    (d) causing the defibrillator to deliver a defibrillation shock to the patient via the electrodes if the shockable heart rhythm is detected.

28. The method of claim 27, further comprising causing the defibrillator to instruct the user to initiate shock delivery when the shockable heart rhythm is detected.

29. The method of claim 27, further comprising causing the defibrillator to deliver the defibrillation shock automatically when the shockable heart rhythm is detected.

30. The method of claim 27, further comprising causing the defibrillator to notify an emergency response system.

31. The method of claim 27, further comprising causing the defibrillator to instruct the user to notify an emergency response system.

32. The method of claim 27, wherein the defibrillator visually instructs the user.

33. The method of claim 27, wherein the defibrillator aurally instructs the user.

34. The method of claim 27, wherein the defibrillator both visually and aurally instructs the user.

35. A computer-readable medium having a computer-executable user interface component for generating graphical instructions for a user which illustrate to the user how to treat a patient during an emergency using the defibrillator, including how to attach a set of defibrillation electrodes to the patient.

36. The user interface component of claim 35, wherein the graphical instructions which illustrate to the user how to treat the patient during an emergency include graphical instructions for operating the defibrillator.

37. The user interface component of claim 36, wherein the graphical instructions for operating the defibrillator further include graphical instructions for the user to initiate delivery of a defibrillation shock if a shockable heart rhythm is detected.

38. The user interface component of claim 35, wherein the graphical instructions for operating the defibrillator include graphical instructions for administering CPR to the patient.

39. The user interface component of claim 38, wherein the graphical instructions for administering CPR to the patient include graphical instructions to assess the patient's condition.

40. The user interface component of claim 39, wherein the graphical instructions to assess the patient's condition include graphical instructions to check the patient's breathing, check the patient's pulse, and deliver rescue breaths if appropriate.

41. The user interface component of claim 35, wherein the user interface component further generates aural instructions for the user which demonstrate to the user how to treat a patient during an emergency using the defibrillator.

42. A computer-readable medium having a computer-executable user interface component for generating aural instructions for a user which demonstrate to the user how to treat a patient during an emergency using the defibrillator, including how to administer CPR to the patient, wherein the aural instructions which demonstrate how to administer CPR to the patient comprise instructions to assess the patient's condition by checking the patient's breathing, checking the patient's pulse, and delivering rescue breaths if appropriate.

43. The user interface component of claim 42, wherein the aural instructions which demonstrate to the user how to treat the patient during an emergency include aural instructions for operating the defibrillator.

44. The user interface component of claim 43, wherein the aural instructions for operating the defibrillator include aural instructions for attaching a set of defibrillation electrodes to the patient.

45. The user interface component of claim 44, wherein the aural instructions for operating the defibrillator further include aural instructions for the user to initiate delivery of a defibrillation shock if a shockable heart rhythm is detected.

46. The user interface component of claim 42, wherein the aural instructions for operating the defibrillator include aural instructions for administering CPR to the patient.

47. The user interface component of claim 42, wherein the user interface component further generates graphical instructions for the user which illustrate to the user how to treat a patient during an emergency using the defibrillator.

* * * * *